United States Patent [19]
Kling

[11] Patent Number: 5,201,725
[45] Date of Patent: Apr. 13, 1993

[54] NEEDLE FREE I.V. ADAPTER

[75] Inventor: John E. Kling, San Diego, Calif.

[73] Assignee: IVAC, San Diego, Calif.

[21] Appl. No.: 765,807

[22] Filed: Sep. 26, 1991

[51] Int. Cl.[5] .............................................. A61M 27/00
[52] U.S. Cl. ..................................... 604/284; 604/82; 251/342
[58] Field of Search ........ 604/256, 167, 284, 240–242, 604/246, 249, 82, 83, 239, 241, 283, 905, 34; 251/348, 342

[56] References Cited

U.S. PATENT DOCUMENTS

| | | | |
|---|---|---|---|
| 274,447 | 3/1883 | Kennish | 251/342 |
| 1,189,624 | 7/1916 | Rohrbacher . | |
| 2,755,060 | 7/1956 | Twyman | 251/342 |
| 3,570,484 | 3/1971 | Steer et al. . | |
| 3,837,381 | 9/1974 | Arroyo . | |
| 3,965,925 | 6/1976 | Gooch | 251/342 |
| 3,994,293 | 11/1976 | Ferro | 604/83 |
| 4,009,720 | 3/1977 | Crandall . | |
| 4,013,310 | 3/1977 | Dye . | |
| 4,123,091 | 10/1978 | Cosentino et al. . | |
| 4,143,853 | 3/1979 | Abramson . | |
| 4,324,239 | 4/1982 | Gordon et al. . | |
| 4,436,125 | 3/1984 | Blenkush . | |
| 4,436,519 | 3/1984 | O'Neill . | |
| 4,511,359 | 4/1985 | Vaillancourt . | |
| 4,535,820 | 8/1985 | Raines . | |
| 4,559,043 | 12/1985 | Whitehouse et al. . | |
| 4,559,052 | 12/1985 | Babson . | |
| 4,673,393 | 6/1987 | Suzuki et al. . | |
| 4,720,285 | 1/1988 | Pickhard . | |
| 4,752,292 | 6/1988 | Lopez et al. . | |
| 4,781,698 | 11/1988 | Parren | 604/246 |
| 4,842,591 | 6/1989 | Luther . | |
| 4,895,565 | 1/1990 | Hillstead . | |
| 4,929,235 | 5/1990 | Merry et al. . | |
| 4,932,633 | 6/1990 | Johnson et al. . | |
| 4,946,133 | 8/1990 | Johnson et al. . | |
| 4,960,412 | 10/1990 | Fink . | |
| 4,966,586 | 10/1990 | Vaillencourt . | |
| 4,969,879 | 11/1990 | Lichte . | |
| 4,981,469 | 1/1991 | Whitehouse et al. . | |

OTHER PUBLICATIONS

Health Devices; *NeedleStick-Prevention Devices*, May 1991, vol. 20, No. 5.
Application Ser. No. 07/512,658 by Rogers.

*Primary Examiner*—C. Fred Rosenbaum
*Assistant Examiner*—Manuel Mendez
*Attorney, Agent, or Firm*—Dykema Gossett

[57] ABSTRACT

A medical connector assembly comprises a connector body having a fluid passage there through, a valve member, and means, responsive to a compressive force placed on the medical connector, for permitting a fluid to freely communicate between openings in the connector body. The valve member can be constructed using a single element having a slit therein or it can be constructed using two separate halves which when joined together form an interface slit. In a preferred embodiment, when a compressive force is exerted against the connector body, sufficient distortion is experienced by the valve member to open the slit and permit fluid flow between connector body openings.

26 Claims, 3 Drawing Sheets

NEEDLE FREE I.V. ADAPTER

BACKGROUND OF THE INVENTION

The present invention relates generally to connectors and more specifically relates to connectors for use in introducing medication into a patient and for removing fluids from the patient.

Modern medical practice commonly employs intravenous (I.V.) solutions to administer medications to patients. In most such applications, an intravenous solution flows from an elevated container through tubing which is connected to a needle inserted directly into the patient's vein. Intermittent or "piggy-back" medications are typically added to the intravenous solution at a connector placed in the tubing known as a "Y-site" connector. Y-site connectors generally include a sealed entry port which is integral to the tubing through which fluid flows to (or from) the patient. The sealed entry port of a Y-site connector is typically constructed from a latex plug (generally known as a septum). Medication is introduced into the tubing by penetrating the septum with a secondary needle connected to a syringe or other source of medication. The latex septum is advantageous in that it allows for multiple needle insertions to access a patient's system with no pain or discomfort to the patient. The latex septum is self-healing, and upon removal of the needle the hole through the septum closes thus maintaining a closed system. The self-healing feature of the latex septum as well as its flat surface serve as distinct advantages inasmuch as before and after each needle insertion, the exterior surface of the septum can be easily wiped with alcohol to disinfect the surface and minimize the risk of introducing bacteria and infection to the patient.

One major drawback with the above-referenced conventional practice is that, in addition to the primary needle used to puncture the patient's vein, it necessitates the use of a secondary needle to puncture the septum. Once this secondary needle is exposed to a patient's body fluids it is considered high risk and threatens the health of healthcare workers. Used needles must be handled and disposed of very carefully and the mishandling of used needles accounts for a large percentage of life-threatening injuries to medical personnel.

Several devices have been developed for providing secondary access to a patient's bloodstream without the use of a needle. For example, U.S. Pat. No. 3,570,484 issued to Steer, et al. discloses a device for administering intravenous injections of liquid. U.S. Pat. No. 4,324,239 issued to Gordon, et al. relates to a safety valve for catheterization and is characterized by a piston having an internal flow path. A portion of the piston is surrounded by an elastomeric member which biases the piston in a closed position. Although the above-referenced devices do eliminate the secondary needle connection, and therefore eliminate the risk of needle stick injury to medical personnel, they both present designs which present an unnecessary risk of infection to the patient. This risk is primarily due to the devices are designed with external crevices which promote the pooling of fluid on and around the external surfaces of the device. This pooling effect creates a fluid reservoir during the normal course of using the device. Ideally, a device connected to a patient's bloodstream should not promote pooling during the normal course of its use due to the potential for bacterial infection. If the fluid reservoir or cavity is not clean, bacteria may develop in the reservoir. That bacteria could find its way into a patient's bloodstream when the device is used to administer new medication or to remove fluids from the patient's bloodstream.

In view of the above needs and concerns, there is a need for a needleless connector that is inexpensive to manufacture, disposable, and easily adaptable for use in various medical applications.

Thus it is an object of this invention to eliminate the necessity of using a secondary needle as a component in tubing connections related to intravenous delivery of medication or the removal of fluids from a patient.

It is a further object of this invention to provide a Y-site connector which is easily connectable to a syringe, I.V. administration sets, or other standard medical fittings.

It is still a further object of this invention to provide a Y-site connector which is extremely simply in design, and easy to disinfect.

BRIEF DESCRIPTION OF THE INVENTION

A primary object of the present invention is to provide a medical connector which allows intravenous access to a patient for the infusion or aspiration of fluids. To accomplish this, the medical connector includes a connector body having first and second openings and a first internal wall joining said first and second openings, said first internal wall forming a first fluid passage for communicating a first fluid between said first and second openings. A valve member is disposed in the first fluid passage and is adapted to prevent the first fluid from communicating between the first and second openings through the first fluid passage. Means, responsive to a compressive force placed on the medical connector, functions to permit the first fluid to freely communicate between the first and second openings through the first fluid passage.

The connector body preferably includes a third opening and a second internal wall. The second internal wall connects the third opening to the first fluid passage and forms a second fluid passage for communicating a second fluid between the third opening and the first fluid passage.

The connector body preferably includes a relieved portion thereby improving the responsiveness of the medical connector to the compressive force placed on it. The relieved portion is preferably located proximate the first opening of the connector body.

In a preferred embodiment, the flow permitting means includes a slit passing through the valve member. The valve member is preferably disposed in the first fluid passage proximate the first opening. The valve member includes a fluid delivery mating surface which extends beyond the first opening making the fluid delivery mating surface easy to clean.

In an alternative embodiment, the valve member is comprised of two separate halves, each half including a mating surface, and each half adapted to contact one another along their mating surfaces, and the mating surfaces forming an interface slit between the valves halves wherein the flow permitting means includes the interface slit between the valve halves. Preferably, the connector body includes first and second relieved portions, wherein the valve member is disposed between the first and second relieved portions. Preferably the slit in the valve (or the slit between the valve halves) is generally planar and resides in a plane which is generally perpendicular to a line passing through the first and second relieved portions of the connector body.

Preferably, the medical connector further includes a female fastener adapted to engage and compress the medical connector thereby activating the flow permitting means and allowing the first fluid to communicate between the first and second openings through the first fluid passage. The female fastener preferably includes thread means for threadedly engaging the connector body portion of the medical connector. In a first embodiment of the female fastener, thread means are provided having a bore disposed in the female fastener which has sloping, concentric sidewalls. In a second embodiment of the female fastener thread means is provided including a bore disposed in the female fastener wherein the bore has non-concentric sidewalls. Both of the above embodiments of the female fastener are effective for threadedly engaging and compressing the medical connector to activate the flow permitting means.

Both the female fastener and the valve member preferably include fluid delivery mating surfaces and the female fastener preferably includes a fluid delivery passage which terminates at the fastener fluid delivery mating surface. When the female fastener engages and compresses the medical connector body, the fluid delivery mating surface of the female fastener and the valve member are pressingly engaged thereby allowing the first fluid to communicate between the fluid delivery passage of the female fastener and the first fluid passage of the connector body across the fluid delivery matching surfaces. The fluid delivery mating surfaces of the female fastener and the valve are preferably generally plainer for superior sealing capability and ease of disinfection.

DETAILED DESCRIPTION OF THE PREFERRED EMBODIMENTS

Figure 1:
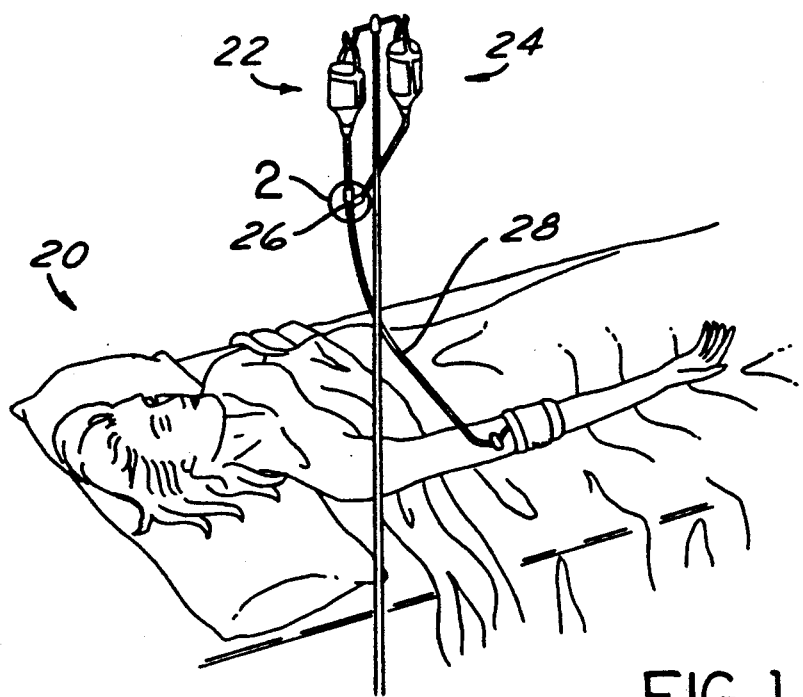
FIG. 1 is an isometric view of a patient being administered medication intravenously using the medical connector of the present invention.

Now referring to FIG. 1, patient 20 is shown being administered intravenous (I.V.) fluid. This intravenous fluid is comprised of two solutions. The two solution, housed and container 24, is generally know as an intravenous solution (also called parenteral liquid). The second solution is housed in container 22 and is generally known as the "piggy-back" medication. These two solutions are combined at Y site connector 26 and flow through tube 28 into a vein of patient 20.

Figures 2, 3, 4:
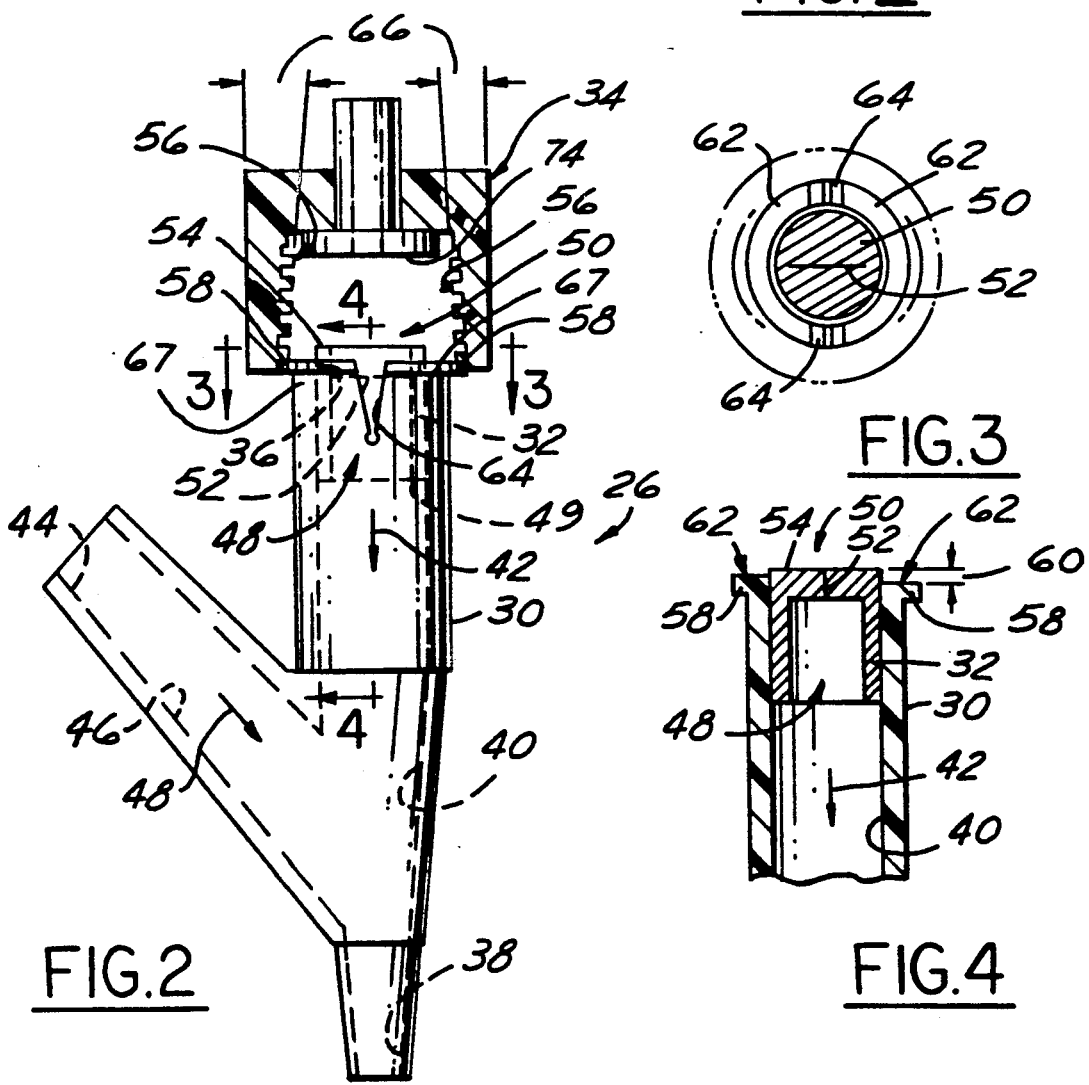
FIG. 2 is an enlarged cross-sectional view of the medical connector located within encircled portion 2 of FIG. 1.
FIG. 3 is a cross-sectional top view of the medical connector of the present invention taken substantially along lines 3—3 of FIG. 2.
FIG. 4 is a partial cross-sectional side view of the medical connector of the present invention taken substantially along lines 4—4 of FIG. 2.

Now referring to FIG. 2, medical connector 26 is comprised of three components —connector body 30, valve member (or elastic plug) 32, and threaded collar (or female fastener) 34. Connector body 30 includes openings 36, 38 and a first internal wall 40 which forms a first fluid passage 42 between openings 36, 38. First fluid passage 42 allows a first fluid to communicate between opening 36 and 38. Medical connector 26 also includes third opening 44 and second internal wall 46. Second internal wall 46 communicates between third opening 44 and first internal wall 40 to from a second fluid passage 48 for communicating a second fluid between third opening 44 and first fluid passage 42.

Valve member 32 is preferably constructed from an elastomer material which is easily deformable. Valve 32 resides within first fluid passage 42 preferably approximate opening 36. In a first embodiment of valve member 32, it is preferably constructed having a hollow center area 48 which opens into first fluid passage 42 by way of a lower opening 49. Upper portion 50 of valve member 32 completely bridges hollow center area 48 thereby sealing first fluid passage 42 from bacterial exposure through opening 36. Upper portion 50 of valve 32 includes vertical slit 52. Vertical slit 52 is preferably placed through upper portion 50 of valve 32 such that it spans between sealing surface 54 and hollow center area 48.

Now referring to FIGS. 2 and 3, in a first embodiment, threaded collar 34 is configured with internal threads 56 which are adapted to threadedly engaged ears 58 of connector body 30. Prior to threadedly engaging threaded collar 34 to ears 58, slit 52 is closed as generally shown in FIG. 3. In its closed position, slit 52 does not permit liquids, bacteria or the like from travelling from sealing surface 54 into first fluid passage 42. Thus, it can be seen that when slit 52 is closed, valve 32 acts to block the entrance of fluid, bacteria or the like into first fluid passage 42. Valve 32 is preferably disposed within first fluid passage 42 such that sealing surface 54 is slightly raised 60 above shoulder 62 of connector body 30. This raised relationship allows sealing surface 54 and shoulder 62 to be easily disinfected by way of alcohol swab or the like. Additional, by raising sealing surface 54 slightly above shoulder 62, threaded collar 34 easily seals against sealing surface 54 thereby providing a fluid tight seal between collar 34 and connector body 30. This sealing feature of the present invention will be more fully explained in conjunction with FIG. 5.

Connector body 30 is preferably fitted with relieved portions 64. Relieved portions 64 are preferably placed in connector body 30 approximate opening 36 and function to allow sidewall 67 of connector body 30 to more easily collapse inwardly as threaded collar 34 is threadedly engaged to ears 58.

Internal threads 56 of threaded collar 34 are designed having an inward taper 66. The function of inward taper 66 will now be described in conjunction with FIG. 5.

Figure 5:
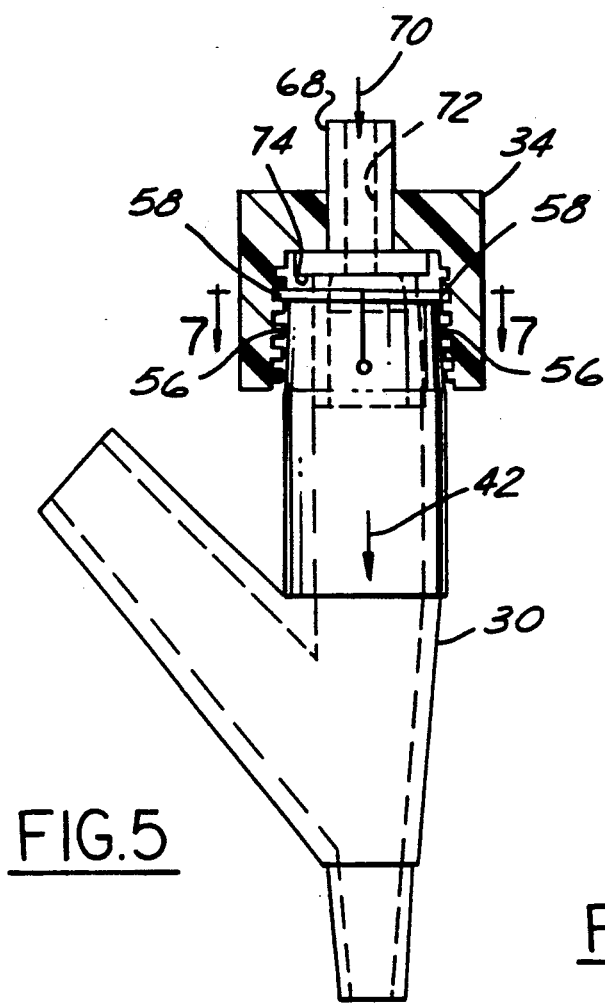
FIG. 5 depicts the medical connector of FIG. 2 showing the threaded collar fully engaged and compressing the connector body.
Figure 6:
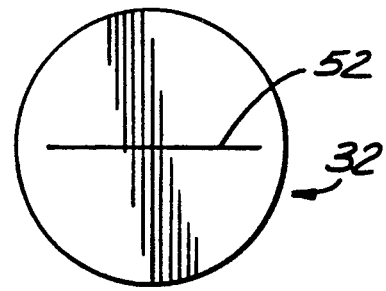
FIG. 6 is a diagrammatic top view of the elastic plug when the medical connector is not compressed.
Figure 7:
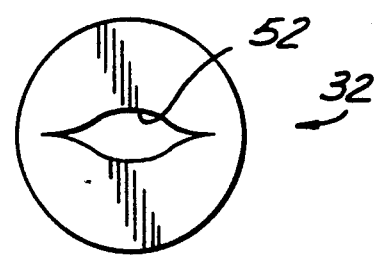
FIG. 7 is a diagrammatic top view of the elastic plug of FIG. 7 wherein the medical connector is compressed.

Now referring to FIG. 5, when it is desired to introduce an intravenous fluid into first fluid passage 42 through tube 68, threaded collar 34 is threadedly engaged to ears 58 of connector body 30. Because internal threads 56 of collar 34 are designed with inward taper 66, threaded collar exerts a compressive force on ears 58 as it is threaded onto connector 30. Prior to threading collar 34 onto body 30, slit 52 is closed as shown in FIG. 6. However, once threaded collar 34 is fully engaged to connector body, the inward compressive forces applied to ears 58 by tapered threads 56, deform valve 32 thereby opening slit 52 as shown in FIG. 7. When slit 52 is opened as shown in FIG. 7, fluid 70 introduced into passage 72 of tube 68 is free to flow through open slit 52 and into first fluid passage 42 for delivery to patient 20. Sealing surface 74 of collar 34 and sealing surface 54 of valve 32 (see FIG. 2) are preferably generally flat thereby providing an excellent mating and sealing surface when collar 34 is threadedly engaged onto connector body 30.

Thus, in view of the above description, it is easily seen how the medical connector of the present invention provides for a normally closed valve when threaded collar 34 is not present and also utilizes the threaded collar 34 to provide a means for introducing an intravenous fluid to a patient with minimum risk of infection and without the danger associated with needles.

Figure 8:
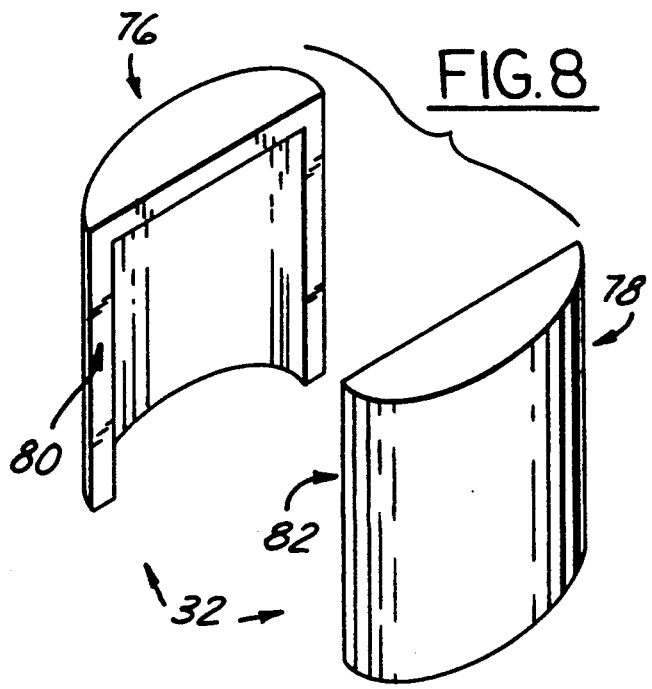
FIG. 8 is an isometric view of a second embodiment of the elastic plug of the present invention.
Figure 9:
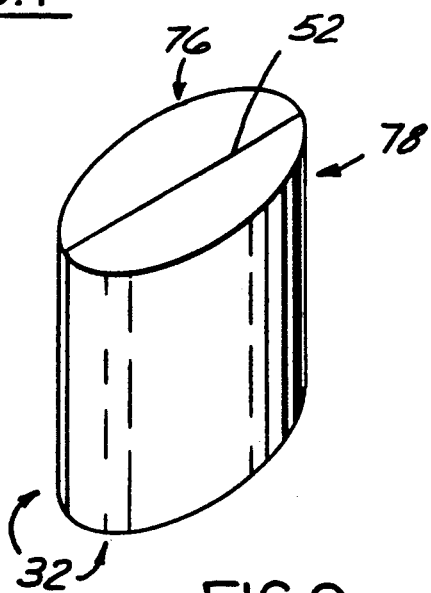
FIG. 9 is an isometric view of the second embodiment of the elastic plug of the present invention showing the relative orientation of two plug halves which exists when they reside within the connector body.

Now referring to FIGS. 8 and 9, a second embodiment of the valve member 32 includes valve halves 76, 78. Valve halves 76, 78 function in the identical manner as that described in conjunction with single unit valve member 32. They provide an alternate means of construction and fabrication of the valving mechanism which may be more suited for high volume production than that of the first embodiment. Valve halves 76, 78 are designed with matching faces 80, 82 which when brought together (see FIG. 9) form slit 52. Slit 52 of FIG. 9 functions in the identical manner as has been described in conjunction with FIG. 2 through FIG. 7.

Figure 10:
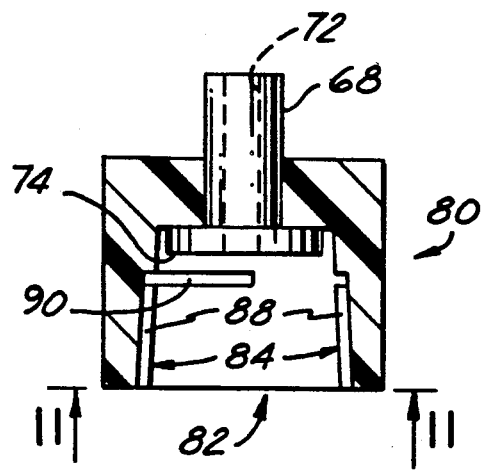
FIG. 10 is a cross-sectional view of a second embodiment of the threaded collar of the present invention.
Figure 11:
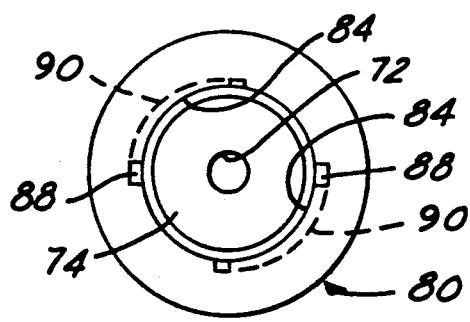
FIG. 11 is a bottom view of the second embodiment of the threaded collar of the present invention taken substantially along lines 11—11 of FIG. 10.
Figure 12:
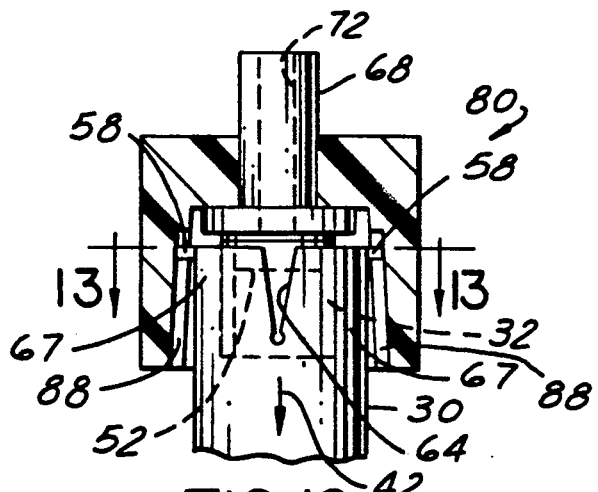
FIG. 12 is a cross-sectional view of the medical connector of the present invention utilizing the embodiment of the threaded connector of FIG. 10.
Figure 13:
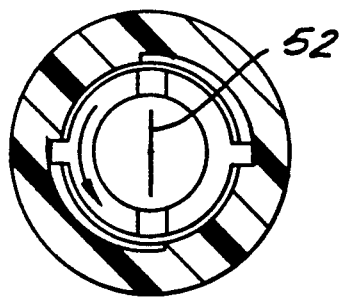
FIG. 13 is a diagrammatic top view of the elastic plug of the present invention taken substantially along lines 13—13 of FIG. 12.
Figure 14:
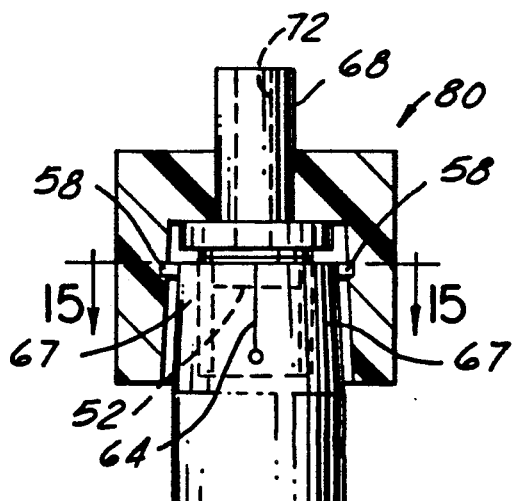
FIG. 14 is a depiction of the medical connector of FIG. 12 wherein the threaded connector is rotated 90°.

Now referring to FIG. 10, in an alternative embodiment of threaded collar 34 (FIGS. 2 and 5), threaded collar 80 is provide with central bore 82 and generally cylindrical sidewalls 84. Disposed within generally cylindrical sidewalls 84 are groves 88. Near the upper portion 90 of groves 88, they alter their direction and no longer run generally parallel to the axis of central bore 82 but rather form non-concentric, arcuate groves 90 within sidewalls 84 of collar 80. Non-concentric groves 90 provide means for compressing ears 58 of connector body 30. This function will now be described in conjunction with FIGS. 12-15.

Figure 15:
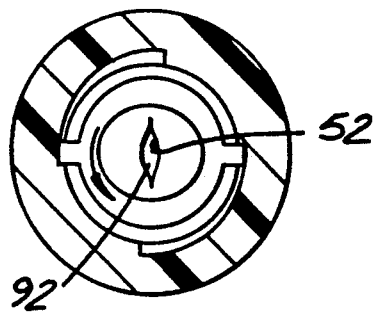
FIG. 15 is a diagrammatic top view of the medical connector of the present invention taken substantially along lines 15—15 of FIG. 14.

Now referring to FIGS. 12-15, when threaded collar 80 does not reside on connector body 30, slit 52 is closed (see FIG. 13), as heretofore has been explained. When it is desired to administer an I.V. fluid through passage 72 of tube 68, threaded collar 80 is placed over connector body 30 such that ears 58 align with groves 88. Once this alignment has been achieved, threaded collar 80 is pushed towards connector body 30 and then rotated approximately 90°. Because grooves 90 are non-concentric, the 90° rotation of collar 80 exerts an inward compressive force on ears 58 thereby inwardly displacing walls 67 of connector body 30 and opening slit 52 as shown in FIG. 15. Walls 67 are fitted with relieved portion 64 so that they are easily compressed upon rotating threaded collar 80. Preferably, slit 52 is generally plannar and lies in a plane which is generally perpendicular to a line which passes through opposing recesses 64. This construction is preferably in that it creates the greatest opening 92 for a given displacement of wall 67.

The foregoing detained description shows that the preferred embodiments of the present invention are well suited to fulfill the objects of the invention. It is recognized that those skilled in the art may make various modifications or additions to the preferred embodiments chosen here to illustrate the present invention, without departing from the spirit of the present invention. For example, it is contemplated that the medical connector of the present invention can be modified to interface to any number of standard medical-type connectors. It is also contemplated that the medical connector of the present invention can be constructed from any wide range of materials which are not reactive to chemicals found in medications, body fluids, or the like. According, it is to be understood that the subject matter sought to be afforded protection hereby should be deemed to extend to the subject matter defined in the appended claims, including all fair equivalents thereof.

I claim:

1. A medical connector comprising:
    a connector body having first and second openings and a first internal wall joining said first and second openings, first internal wall forming a first fluid passage for communicating a first fluid between said first and second openings,
    a valve member disposed in said first fluid passage, said valve member adapted to prevent said first fluid from communicating between said first and second openings through said first fluid passage,
    flow permitting means, responsive to a compressive force placed on said medical connector, for permitting said first fluid to freely communicate between said first and second openings through said first fluid passage;
    said connector body further comprises a third opening and a second internal wall, said second internal wall joining said third opening to said first fluid passage, said second internal wall forming a second fluid passage for communicating a second fluid between said third opening and said first fluid passage, and
    further including a female fastener adapted to engage and compress said medical connector thereby activating said flow permitting means and allowing said first fluid to communicate between said first and second openings through said first fluid passage.

2. The medical connector of claim 1, wherein said connector body includes a relieved portion thereby improving the responsiveness of said medical connector to said compressive force placed on said medical connector.

3. The medical connector of claim 2, wherein said relieved portion of said connector body is located proximate said first opening of said connector body.

4. The medical connector of claim 1, wherein said flow permitting means includes a slit passing through said valve member.

5. The medical connector of claim 1, wherein said valve member is disposed in said first fluid passage proximate said first opening.

6. The medical connector of claim 5, wherein a portion of said valve member extends beyond said first fluid passage and includes a fluid delivery mating surface.

7. The medical connector of claim 1, wherein said valve member is comprised of an elastomer material.

8. The medical connector of claim 1, wherein said valve member is comprised of two separate halves, each said half including a mating surface, said valve halves adapted to contact one another along their mating surfaces, said contact between said mating surfaces forming an interface slit between said valve halves wherein said flow permitting means includes said interface slit between said valve halves.

9. The medical connector of claim 1, wherein said connector body includes first and second relieved portions, and wherein said valve member is disposed between said first and second relieved portions.

10. The medical connector of claim 9, wherein said flow permitting means includes a generally planar slit passing through said valve member, and wherein said plane of said slit is generally perpendicular to a line passing through said first and second relieved portions of said connector body.

11. The medical connector of claim 1, wherein said female fastener includes thread means for threadedly engaging said connector body portion of said medical connector.

12. The medical connector of claim 11, wherein said thread means includes a bore disposed in said female fastener, said bore having a sloping, concentric side walls.

13. The medical connector of claim 11, wherein said thread means includes a bore disposed in said female fastener, said bore having non-concentric side walls.

14. The medical connector of claim 1, wherein said female fastener and said valve member both include fluid delivery mating surfaces, and wherein said female fastener includes a fluid delivery passage which terminates at said fastener fluid delivery mating surface whereby when said female fastener engages and compresses said medical connector body, said fluid delivery mating surfaces of said female fastener and said valve member are pressingly engaged, thereby allowing said first fluid to communicate between said fluid delivery passage of the female fastener and said first fluid passage of the connector body.

15. The medical connector of claim 14, wherein said fluid delivery mating surface of said female fastener and said valve member are generally planar.

16. A medical connector comprising:
a connector body having first and second openings and a first internal wall joining said first and second openings, said first internal wall forming a first fluid passage for communicating a first fluid between said first and second openings,
a valve member disposed in said first fluid passage, said valve member adapted to prevent said first fluid from communicating between said first and second openings through said first fluid passage;
female fastener adapted to engage and compress said medical connector; flow permitting means, responsive to a compressive force placed on said medical connector by said female fastener, for permitting said first fluid to freely communicate between said first and second openings through said first fluid passage, and
said connector body further comprises a third opening and a second internal wall, said second internal wall joining said third opening to said first fluid passage, said second internal wall forming a second fluid passage for communicating a second fluid between said third opening and said first fluid passage.

17. The medical connector of claim 16, wherein said connector body includes a relieved portion thereby improving the responsiveness of said medical connector to said compressive force placed on said medical connector and wherein said relieved portion of said connector body is located proximate said first opening of said connector body.

18. The medical connector of claim 16 wherein said flow permitting means includes a slit passing through said valve member.

19. The medical connector of claim 16, wherein said valve member is disposed in said first fluid passage proximate said first opening and wherein a portion of said valve member extends beyond said first fluid passage and includes a fluid delivery mating surface.

20. The medical connector of claim 16, wherein said valve member is comprised of an elastomer material.

21. The medical connector of claim 16, wherein said valve member is comprised of two separate halves, each said half including a mating surface, said valve halves adapted to contact one another along their mating surfaces, said contact between said mating surfaces forming an interface slit between said valve halves wherein said flow permitting means includes said interface slit between said valve halves.

22. The medical connector of claim 16, wherein said connector body includes first and second relieved portions, and wherein said valve member is disposed between said first and second relieved portions and wherein said flow permitting means includes a generally planar slit passing through said valve member, and wherein said plane of said slit is generally perpendicular to a line passing through said first and second relieved portions of said connector body.

23. The medical connector of claim 16, wherein said female fastener includes thread means for threadedly engaging said connector body portion of said medical connector.

24. The medical connector of claim 23, wherein said thread means includes a bore disposed in said female fastener, said bore having sloping, concentric side walls.

25. The medical connector of claim 23, wherein said thread means includes a bore disposed in said female fastener, said bore having non-concentric side walls.

26. The medical connector of claim 16, wherein said female fastener and said valve member both include fluid delivery mating surfaces, and wherein said female fastener includes a fluid delivery passage which terminates at said fastener fluid delivery mating surface whereby when said female fastener engages and compresses said medical connector body, said fluid delivery mating surfaces of said female fastener and said valve member are pressingly engaged, thereby allowing said first fluid to communicate between said fluid delivery passage of the female fastener and said first fluid passage of the connector body and wherein said fluid delivery mating surface of said female fastener and said valve member are generally planar.

* * * * *

UNITED STATES PATENT AND TRADEMARK OFFICE
CERTIFICATE OF CORRECTION

PATENT NO. : 5,201,725
DATED : April 13, 1993
INVENTOR(S) : Kling

It is certified that error appears in the above-identified patent and that said Letters Patent is hereby corrected as shown below:

Col. 7, line 68, insert a paragraph before, "flow permitting means,".

Signed and Sealed this

Eighteenth Day of January, 1994

Attest:

BRUCE LEHMAN

Attesting Officer     Commissioner of Patents and Trademarks